United States Patent [19]

Korthoff

[11] Patent Number: 4,534,352
[45] Date of Patent: Aug. 13, 1985

[54] SURGICAL FASTENER MEMBER HAVING INCREASED RATE OF ABSORPTION

[75] Inventor: Herbert W. Korthoff, Wilton, Conn.

[73] Assignee: United States Surgical Corporation, Norwalk, Conn.

[21] Appl. No.: 538,982

[22] Filed: Oct. 4, 1983

[51] Int. Cl.³ .............................................. A61B 17/08
[52] U.S. Cl. ............................. 128/334 C; 227/DIG. 1
[58] Field of Search ............... 128/334 R, 334 C, 335, 128/337, 325, 326; 227/DIG. 1; 411/462, 463, 349, 469

[56] References Cited

U.S. PATENT DOCUMENTS

| | | |
|---|---|---|
| 2,014,746 | 9/1935 | Robergel ..................... 411/452 X |
| 3,166,072 | 1/1965 | Sullivan, Jr. |
| 3,258,012 | 6/1966 | Nakayama et al. |
| 3,403,592 | 10/1968 | Larson |
| 3,595,201 | 7/1971 | Oudenhoven |
| 3,598,299 | 8/1971 | Johnson |
| 3,641,804 | 2/1972 | Oudenhoven |
| 3,744,495 | 7/1973 | Johnson |
| 3,869,957 | 3/1975 | Barth et al. |
| 3,879,783 | 4/1975 | Giulie |
| 3,899,914 | 8/1975 | Akiyama |
| 3,924,629 | 12/1975 | Akiyama |
| 3,926,193 | 12/1975 | Hasson |
| 4,060,089 | 11/1977 | Noiles |
| 4,278,091 | 7/1981 | Borzone |
| 4,434,796 | 3/1984 | Karapetian et al. ................ 128/335 |

FOREIGN PATENT DOCUMENTS

| | | |
|---|---|---|
| 01190 | 4/1983 | PCT Int'l Appl. ........... 227/DIG. 1 |
| 713384 | 8/1954 | United Kingdom . |
| 972731 | 10/1964 | United Kingdom . |

Primary Examiner—Michael H. Thaler
Attorney, Agent, or Firm—John E. Nathan; Jeffrey H. Ingerman

[57] ABSTRACT

A surgical fastener member of an absorbable resinous material is disclosed. The prong or prongs of the fastener member have an increased surface area to volume ratio, giving the fastener an increased rate of absorption in the body. Each prong is formed with a shank having a total surface area which is at least about 25% greater than the total surface area of an equivalent shank of constant circular radial cross section having a volume equal to the volume of the disclosed shank. Also, the ratio of the smaller to the larger of the slenderness ratios about any two perpendicular axes in the radial shank cross section is in the range of from about 0.67:1.0 to 1.0:1.0, along substantially the entire length of the shank. Preferably, the shank has a central core whose radial cross-sectional area is from about 15% to about 50% of the total radial cross-sectional area and a plurality of fins projecting outward from the core and extending substantially longitudinally along substantially the entire length of the shank.

5 Claims, 15 Drawing Figures

SURGICAL FASTENER MEMBER HAVING INCREASED RATE OF ABSORPTION

BACKGROUND OF THE INVENTION

This invention relates to surgical fasteners (e.g., staples), and more particularly to surgical fastener members which are absorbed by the body at an increased rate.

Surgical fastening devices allow a surgeon to fasten body tissue by applying surgical fasteners. The fasteners may be applied singly in succession or a number may be applied simultaneously. Surgical fasteners are often made of metals such as tantalum or stainless steel, which are inert. Fasteners of magnesium, which fasteners are gradually absorbed by the body, are also known.

Non-metallic fasteners are also known and may in some cases have certain advantages over metal fasteners. For example, metal fasteners in the body may scatter X-rays and may therefore degrade the quality of radiographs.

This problem does not arise with fasteners of non-metallic resinous materials. Such resinous surgical fasteners are usually made of two parts: a fastener member which pierces the tissue from one side and a retainer member which interlocks with the fastener member on the other side of the tissue. As used herein, the term "resinous materials" means non-metallic materials, such as natural or synthetic polymers and resins, including protein-based materials, which are relatively flexible and elastic, and which are absorbable by the body. One resinous fastener structure and apparatus for applying it are disclosed in Green U.S. Pat. No. 4,402,445, issued Sept. 6, 1983, which is hereby incorporated by reference in its entirety.

It is generally desirable to eliminate absorbable fasteners from the body promptly. On the other hand, absorbable fasteners must be absorbed slowly enough to retain their tensile strength for a time sufficient to allow the fastened tissue to heal. Desirably the fasteners are also stiff enough to penetrate tissue without the aid of metal assist pins or the like in the fastener-applying apparatus.

Thus, the need exists for resinous fasteners having an increased rate of absorption in the body, but with sufficient retention of tensile strength during absorption and with sufficient columm stiffness to penetrate tissue without buckling.

SUMMARY OF THE INVENTION

This need is met by the absorbable surgical fastener of the present invention, which fastener has a specially shaped fastener member with an increased ratio of surface area to volume as compared to the surface area to volume ratios of known fastener members. The fastener member comprises (1) a base (or crown) and (2) at least one prong (or leg) extending substantially perpendicularly from the base and having (a) a shank which is joined at its proximal end to the base and (b) a barb at the distal end of the shank for penetrating the tissue.

The total surface area of the shank of this invention is at least 25% greater than the total surface area of an equivalent shank of constant circular radial cross section having a volume equal to the volume of the shank of this invention. (As used herein, the term "radial cross section" means a cross section in a plane perpendicular to the longitudinal axis of the shank.) Along substantially the entire length of the shank, the ratio of the slenderness ratios about any two perpendicular axes in the radial shank cross section is in the range of from about 0.67:1.0 to about 1.0:1.0. Preferably, along substantially its entire length, the shank has (1) a core whose area is from about 15% to about 50% of the total radial shank cross-sectional area and (2) a plurality of fins projecting radially outward from the core and extending substantially longitudinally along the shank.

A preferred absorbable fastener material is disclosed in copending, commonly-assigned Kaplan et al. U.S. patent application Ser. No. 436,056, filed Oct. 22, 1982, hereby incorporated by reference in its entirety.

Thus, an absorbable fastener member is provided which has an increased rate of absorption in the body as compared to known fastener members, but which retains sufficient tensile strength during absorption to allow healing to occur. The fastener member also has sufficient column stiffness to penetrate tissue without buckling.

BRIEF DESCRIPTION OF THE DRAWINGS

The above and other advantages of the present invention will be more apparent after consideration of the accompanying drawings in which like parts are indicated by like reference characters throughout and in which.

DETAILED DESCRIPTION OF THE INVENTION

It has been found that the rate of absorption of absorbable resinous fastener members can be increased by increasing the ratio of surface area to volume of the fastener member shanks. This ratio is equal to the ratio of perimeter to area of the radial cross section of the shank, for a shank of constant radial cross section.

Figure 1:
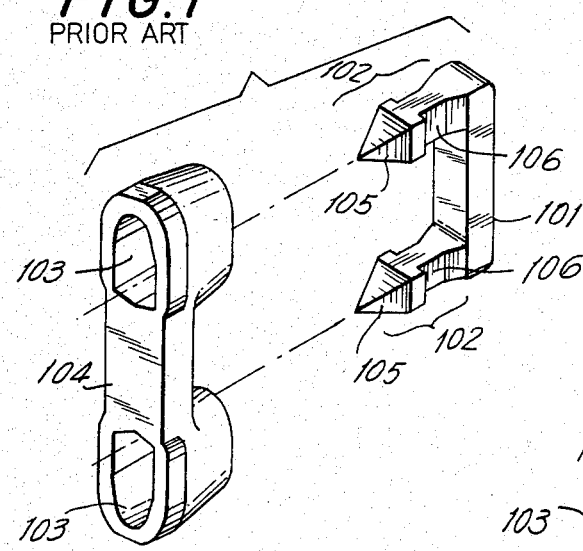
FIG. 1 is an exploded perspective view of a known individual surgical fastener.

A known surgical fastener of resinous material is shown in FIG. 1. The fastener comprises retainer member 104 and fastener member 101, which has two prongs 102 that are driven through tissue (not shown) to engage apertures 103 in retainer member 104. Prongs 102 each include a barb 105 attached to a shank 106.

Figure 2:
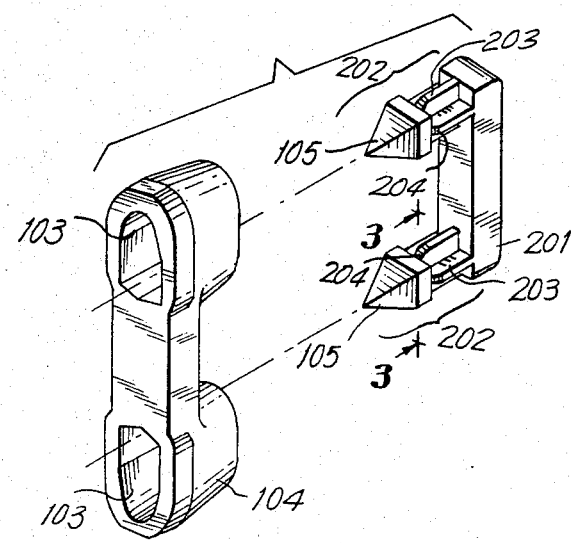
FIG. 2 is an exploded perspective view of a surgical fastener having a preferred fastener member according to the present invention.
Figure 3:
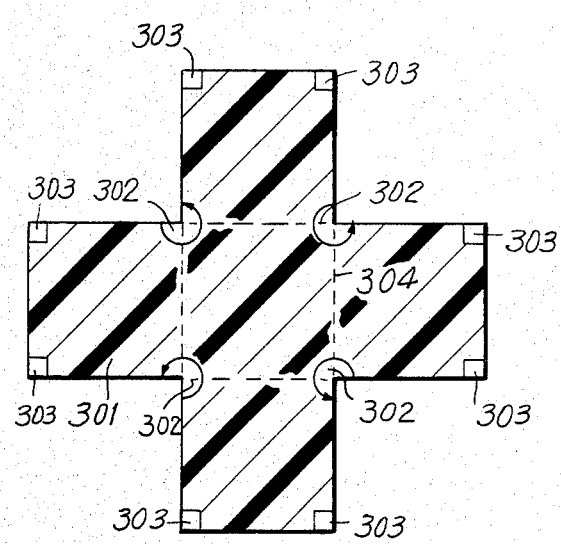
FIG. 3 is a radial cross-sectional view of a preferred fastener member shank according to the present invention taken along line 3—3 of FIG. 2.
Figure 4:
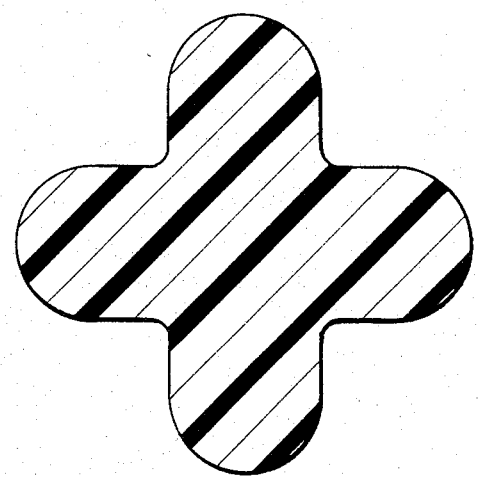
FIGS. 4 through 10 are radial cross-sectional views of other fastener member shanks according to the present invention.
Figure 5:
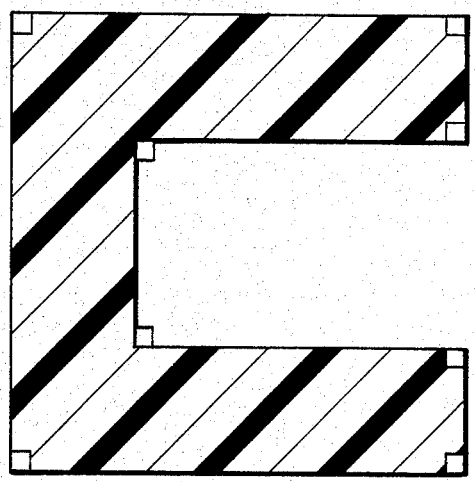
Figure 6:
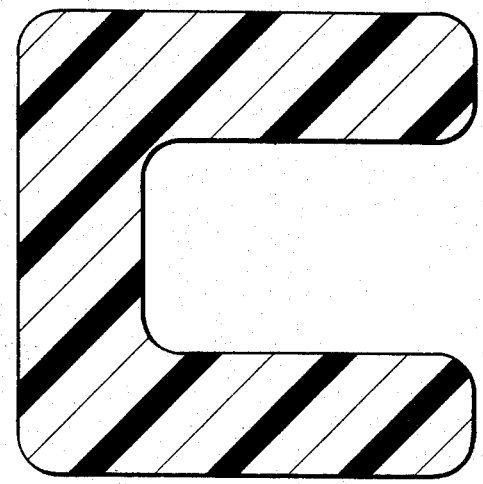
Figure 7:
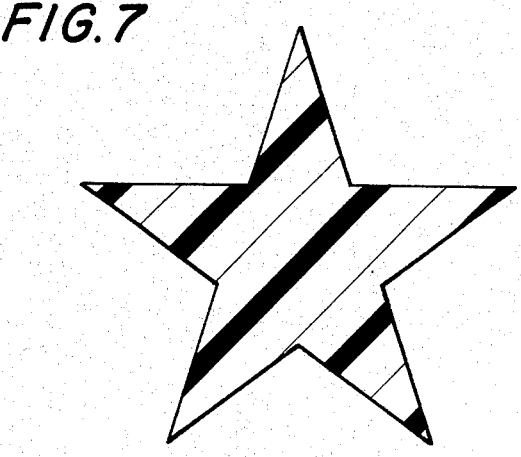
Figure 8:
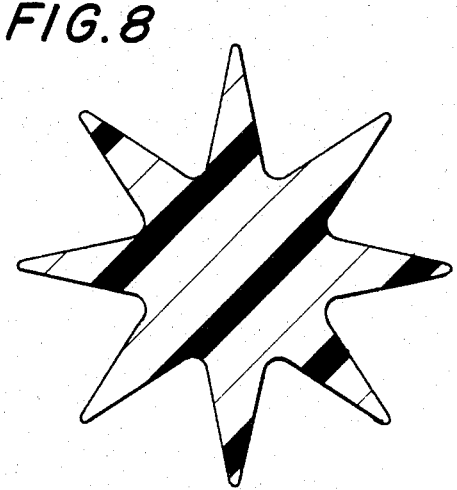
Figure 9:
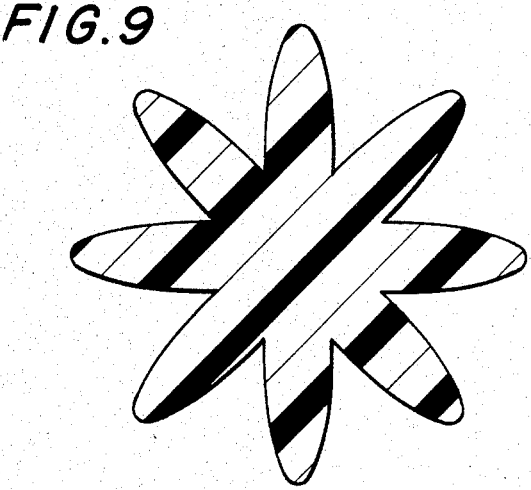
Figure 10:
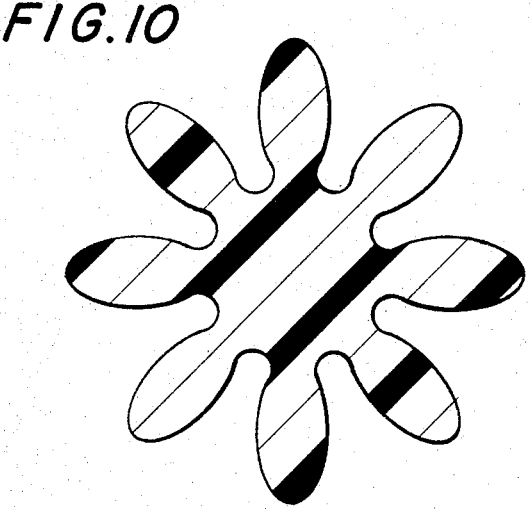
Figure 11:
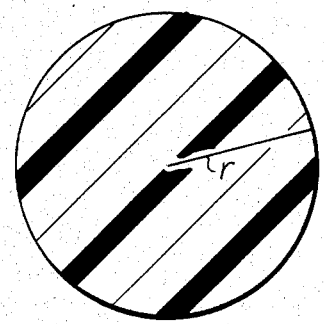
FIGS. 11 through 14 are radial cross-sectional views of fastener member shanks within (in the case of FIGS. 13 and 14) and without (in the case of FIGS. 11 and 12) the scope of the present invention, provided to facilitate discussion of surface area to volume ratio.

FIG. 2 shows a fastener having a preferred fastener member 201 according to the present invention. Prongs 202 of fastener member 201 have barbs 105 at the ends of shanks 203. While known prongs such as prongs 102 of FIG. 1 have shanks with radial cross sections that substantially define figures such as squares and circles, radial cross section 301 of shank 203 is seen in FIG. 3 to define a cruciform (i.e., cross-shaped) figure. This cross section has a core which is the imaginary quadrilateral bounded by dotted line 304. The area of the core is about 20% of the total cross-sectional area.

Other cross-sectional shapes having perimeter to area ratios suitable for fastener member shanks according to this invention are shown in FIGS. 4 through 10. With the exception of the cross sections of FIGS. 5 and 6, all of the cross sections of FIGS. 4 through 10 have a central core and plurality of fins radiating therefrom. Generally, a shank with a central core should not have so large a core that the ratio of surface area to volume is too low. However, the core must be large enough to maintain the strength of the shank during absorption so that healing can occur. Most preferably, a shank of this invention has, along substantially its entire length, (1) a central core whose radial cross-sectional area is from about 15% to about 50% of the total radial cross-sectional area of the shank and (2) a plurality of fins projecting radially outward from the core and extending substantially longitudinally along the shank. For all shanks of this invention that have fins, the fins can extend either parallel to the longitudinal axis of the core or in some other fashion (e.g., helically) which is substantially parallel to the axis.

It is not necessary for the radial shank cross section to be uniform throughout the length of the shank, as long as the cross section has a sufficiently high ratio of perimeter to area at substantially every point along the entire length of the shank. In FIG. 2, for example, each shank 203 narrows at 204 as it approaches barb 105.

For shanks of a given radial cross-sectional area, a shank with a circular cross section will have the minimum cross-sectional perimeter. If the radial cross section of the shank is uniform along the length of the shank, that shank will also have the minimum surface area to volume ratio of any shank having the same volume. It has been found that for a shank for this invention, the surface area to volume ratio should be at least about 25%, and preferably at least about 50%, greater than the surface area to volume ratio for an equivalent shank of constant circular radial cross section having the same volume as the shank of this invention.

Figure 12:
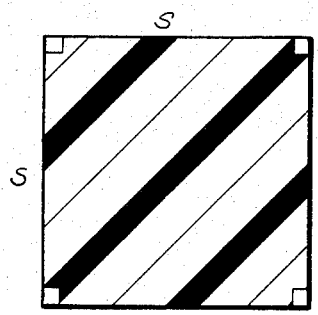
Figure 13:
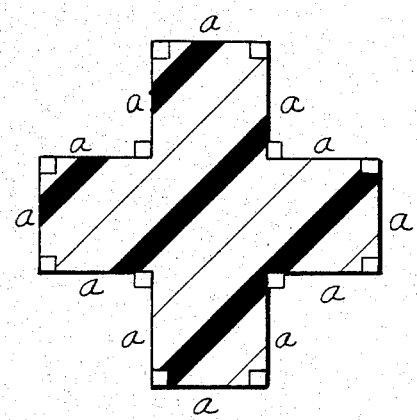
Figure 14:
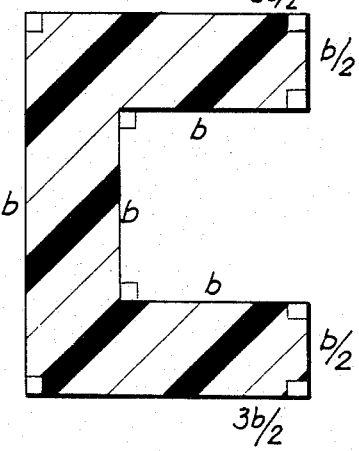

The surface area to volume ratio ($A_s/V$) is calculated in Table I below for four shanks of equal length and constant radial cross section. The radial shank cross sections of the four shanks are shown in FIGS. 11 through 14. The circle in FIG. 11 and the square in FIG. 12 are outside the scope of this invention, because their surface area to volume ratios are too low. FIG. 13 shows a cruciform cross section, and FIG. 14 shows a C-shaped cross section. All four cross sections have the same area $A = \pi r^2$, so that $s = r\sqrt{\pi}$, $a = r\sqrt{(\pi/5)}$, and $b = r\sqrt{(\pi/2)}$.

TABLE I

| Cross Sectional Shape | $A_s/V$ |
|---|---|
| Circle | $2\pi r/\pi r^2 = 2/r$ |
| Square | $4s/s^2 = 4/s = 4/(r\sqrt{\pi})$ $= (4/\sqrt{\pi})/r = 2.26/r$ |
| Cruciform | $12a/5a^2 = 12/5a =$ $= 12/(5(r\sqrt{(\pi/5)}))$ $= (12/\sqrt{(5\pi)})/r$ $= 3.03/r$ |
| C-Shape | $9b/2b^2 = 9/2b = 9/(r\sqrt{2\pi})$ $= (9/\sqrt{(2\pi)})/r$ $= 3.59/r$ |

It can be seen from Table I that the surface area to volume ratio ($A_s/V$) is the lowest for the circular cross section, increasing 13% for the square cross section, 51.5% for the cruciform cross section, and 79.5% for the C-shaped cross section.

Another important consideration in selecting a cross section for a fastener member shank according to this invention is that the shank must have sufficient column stiffness to penetrate tissue without buckling, preferably without the aid of metal assist pins or the like which increase the cost and complexity of fastener-applying apparatus. A parameter frequently used to evaluate column stiffness is the slenderness ratio. For a column of length L, the slenderness ratio for buckling about a particular radial axis is the quotient L/k, where k is the radius of gyration of the column's radial cross section about the particular axis. Formulas for computing the radius of gyration for various cross sections are given at pages 5-30 through 5-33 of *Mark's Standard Handbook for Mechanical Engineers* (T. Baumeister ed., 8th Ed., 1978), which handbook is hereby incorporated by reference in its entirety. For a shank to have sufficient column stiffness to penetrate tissue without buckling, the ratio of the smaller to the larger of the slenderness ratios about any two perpendicular axes in the radial shank cross section should be in the range of from about 0.67:1.0 to 1.0:1.0, and preferably from about 0.75:1.0 to 1.0:1.0.

In addition to the surface area to volume ratio and the ratio of slenderness ratios, other factors—e.g., ease of manufacture—must be considered in the selection of a fastener member shank cross section within the scope of this invention. When all factors are considered, it has been found that the cruciform cross section is the most preferred cross section within the scope of this invention.

Figure 15:
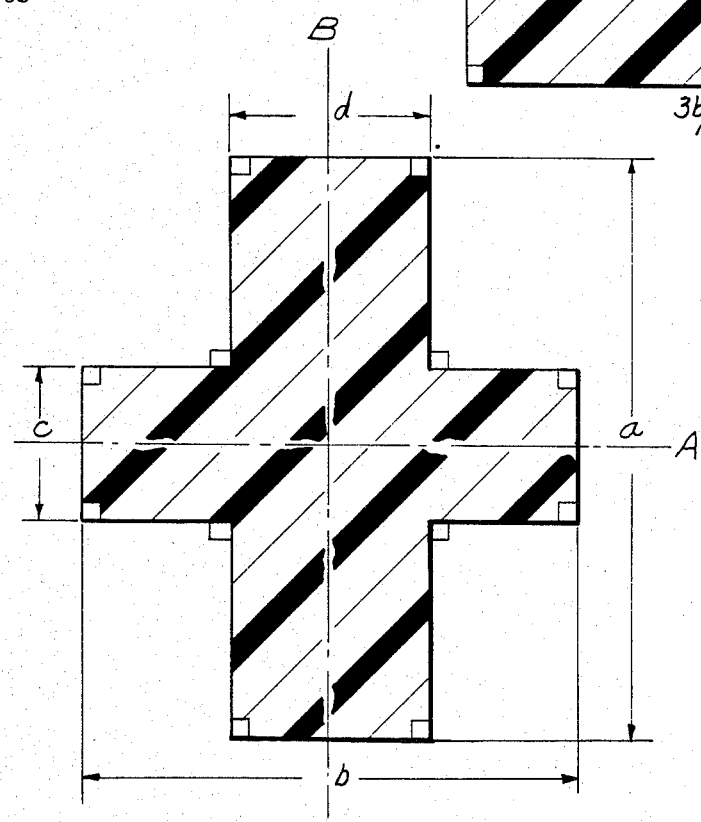
FIG. 15 is a radial cross-sectional view of the most preferred fastener member shank according to the present invention.

A particularly preferred cruciform cross section for a shank of constant radial cross section is illustrated in FIG. 15. Dimension $a = 0.038$ inch, dimension $b = 0.0325$ inch, dimension $c = 0.010$ inch, and dimension $d = 0.012$ inch. For these dimensions, and a shank of length L inch, the slenderness ratio about axis A is L/0.00925 and the slenderness ratio about axis B is L/0.00703. The ratio of slenderness ratios for this particularly preferred embodiment is then $(L/0.00925)/(L/0.00703) = 0.00703/0.00925 = 0.76$. The length of the perimeter is $2(a+b) = 0.141$ inch. For an equivalent circle of equal area, the circumference would be $2\sqrt{(\pi(ad+bc-cd))} = 0.091$ inch. The perimeter to area ratio of the cruciform of FIG. 15 therefore exceeds the circumference to area ratio of the equivalent circle by 54.7%.

In summary, a surgical fastener member is provided which has a sufficiently large surface area to volume ratio (because of its cross section) to have an increased rate of absorption in the body, but yet has sufficient column stiffness to penetrate tissue during normal use, i.e., during application of the fastener to body tissue. One skilled in the art will recognize that the inventive principles disclosed herein can be practiced in other than the embodiments described, and the invention is not limited by those embodiments but only by the claims which follow.

I claim:

1. A surgical fastener member of a resinous material, comprising a base and at least one prong extending substantially perpendicularly from the base, each prong having a shank joined at its proximal end to the base and a barb at the distal end of the shank for penetrating tissue; wherein (1) the radial shank cross section is a cruciform, (2) the total surface area of the shank is about 54.7% greater than the total surface area of an equivalent shank of constant circular radial cross section having a volume equal to the volume of the shank and (3) the ratio of the smaller to the larger of the slenderness ratios about any two perpendicular axes in the radial shank cross section is about 0.76:1.0 along substantially the entire length of the shank.

2. A surgical fastener member of absorbable resinous material, comprising a base and at least one prong extending substantially perpendicularly from the base, each prong having a shank joined at its proximal end to the base and a barb at the distal end of the shank for pentrating tissue; wherein (1) the total surface area of the shank is at least 50% greater than the total surface area of an equivalent shank of constant circular radial cross section having a volume equal to the volume of the shank, (2) the ratio of the smaller to the larger of the slenderness ratios about any two perpendicular axes in the radial shank cross section is in the range of from about 0.67:1.0 to 1.0:1.0 along substantially the entire length of the shank, and (3) the cross section has a central core whose area is from 15% to 50% of the total area thereof and a plurality of projections extending radially outward from the core and spaced equiangularly about the periphery of the core, whereby the rate of absorption of the fastener member is increased as compared to that of a fastener member having said equivalent shank.

3. A surgical fastener member of absorbable resinous material, comprising:
  a base and substantially parallel prongs extending substantially perpendicularly from the base in substantially the same direction, each of the prongs having a shank which is joined at its proximal end to the base and a barb at the distal end of the shank for pentrating tissue, the shank having (1) a longitudinal core along substantially its entire length whose cross-sectional area is from 15% to 50% of the total radial cross-sectional area of the shank and (2) a plurality of fins projecting outward from the core, spaced equiangularly about the periphery of the core, and extending substantially longitudinally along substantially the entire length of the shank, whereby the rate of absorption of the fastener member is increased as compared to that of a fastener member having an equivalent shank of constant circular radial cross section and a volume equal to the volume of the shank.

4. A surgical fastener member of a resinous material, comprising:
  a base and substantially parallel prongs extending substantially perpendicularly from the base in substantially the same direction, each of the prongs having a shank which is joined at its proximal end to the base and a barb at the distal end of the shank for penetrating tissue, the shank having (1) a longitudinal core along substantially its entire length whose cross-sectional area is from about 15% to about 50% of the total radial cross-sectional area of the shank and (2) four fins projecting outward from the core at right angles to each other and extending substantially longitudinally along substantially the entire length of the shank.

5. In combination:
  apparatus for applying surgical fasteners of a resinous material, which are absorbable in the body, each of the fasteners comprising a fastener member and retainer member;
  a plurality of retainer members positioned within the apparatus; and
  a corresponding number of fastener members positioned within the apparatus, each of the fastener members comprising a base and at least one prong extending substantially perpendicularly from the base, each prong having a shank which is joined at its proximal end to the base and a barb at the distal end of the shank for penetrating tissue, wherein (1) the total surface area of the shank is at least 50% greater than the total surface area of an equivalent shank of constant circular radial cross section having a volume equal to the volume of the shank (2) the ratio of the smaller to the larger of the slenderness ratios about any two perpendicular axes in the radial shank cross section is in the range of from about 0.67:1.0 to 1.0:1.0, along substantially the entire length of the shank, and (3) the cross section has a central core whose area is from 15% to 50% of the total area thereof and a plurality of projections extending radially outward from the core and spaced equiangularly about the periphery of the core, whereby the rate of absorption of the fastener member is increased as compared to that of a fastener member having said equivalent shank.

* * * * *